United States Patent [19]

Jones et al.

[11] Patent Number: 4,888,343

[45] Date of Patent: Dec. 19, 1989

[54] PHARMACEUTICAL COMPOSITIONS FOR RELIEF OF DYSMENORRHEA AND/OR PREMENSTRUAL SYNDROME AND PROCESS

[75] Inventors: Howard Jones, Holmdel; Alison B. Lukacsko, West Windsor; Thomas M. Tencza, Wallington; Beth A. Sarsfield, East Brunswick; Mahesh K. Patel, Edison, all of N.J.

[73] Assignee: Bristol-Myers Company, New York, N.Y.

[21] Appl. No.: 907,698

[22] Filed: Sep. 15, 1986

[51] Int. Cl.$^4$ .................... A61K 31/19; A61K 31/52; A61K 31/54; A61K 31/185

[52] U.S. Cl. .................................. 514/264; 514/570; 514/576; 514/223.5

[58] Field of Search ................ 514/576, 570, 225, 264

[56] References Cited

FOREIGN PATENT DOCUMENTS 0081823 6/1983 European Pat. Off. .

OTHER PUBLICATIONS

Welch, Fed. Proc. 44(6) (1985) p. 1840.
Koopmans et al, Eur. J. Clin. Pharmacol. (1987) 31-553-557.

*Primary Examiner*—Stanley J. Friedman
*Attorney, Agent, or Firm*—Charles J. Zeller

[57] ABSTRACT

A pharmaceutical composition for relieving symptoms of dysmenorrhea and/or premenstrual syndrome comprising a combination of aspirin or ibuprofen and a diuretic from the group pamabrom and hydrochlorothiazide; optionally it may also contain an antihistamine.

14 Claims, No Drawings

PHARMACEUTICAL COMPOSITIONS FOR RELIEF OF DYSMENORRHEA AND/OR PREMENSTRUAL SYNDROME AND PROCESS This invention relates to a pharmaceutical composition and process and more particularly to a composition and process of this character which is useful in relieving dysmenorrhea and/or premenstrual syndrome in female subjects.

Pharmaceutical compositions for the treatment of dysmenorrhea and/or premenstrual syndrome are known in the prior art and have been marketed commercially. These, however, have been too complicated in character adding to the expense of such compositions or have lacked as an essential ingredient a non-steroidal anti-inflammatory agent. Thus, for example, a number of commercially available products contain a combination of acetaminophen and pamabrom or a combination of acetaminophen, pamabrom and pyrilamine maleate. The problem with products of this character is that they do not contain a non-steroidal anti-inflammatory agent, such as ibuprofen or aspirin which are highly important but not optimal in relieving the symptoms of dysmenorrhea and/or premenstrual syndrome. The acetaminophen used in such products is an effective analgesic but does not exhibit significant anti-inflammatory properties.

There is at least one commercial product containing a non-steroidal anti-inflammatory such as aspirin that is marketed for use in treating dysmenorrhea and/or premenstrual syndrome. This product has the disadvantage in that it does not contain a highly potent diuretic, another factor which is important in relieving symptoms of dysmenorrhea and/or premenstrual syndrome. This product is a mixture of aspirin, cinnamedrine and caffeine. Cinnamedrine is conventionally recognized as an antispasmodic. Caffeine, although it is recognized as a diuretic is not a highly potent diuretic. Moreover, the latter has the disadvantage of inducing sleeplessness in the subjects to whom it is administered; an important consideration for evening utility.

Rather complex compositions have been suggested in the prior art for use in the treatment of dysmenorrhea and/or premenstrual syndrome. Typical of these teachings are those shown in European Patent Application 82111449.3 which suggests that the typical compositions for treatment of dysmenorrhea comprise combinations of analgesics "(including prostaglandin synthetase inhibitors such aspirin, indomethacin and ibuprofen)", diuretics, antihistamines as well as antispasmadics. The invention of this European Patent Application is said to reside in also incorporating dextromethorphan hydrochloride in these typical combinations. As will be more apparent from the following description the compositions of the present invention are more simplified than those suggested in this reference, thus having a tendency to be less costly than the more complicated formulations suggested in this reference. More importantly, since it involves fewer pharmaceutically active ingredients it avoids the administration of certain drugs that are not necessary for the treatment of dysmenorrhea and/or premenstrual syndrome.

The present invention involves a composition which contains essentially as the only pharmaceutically active ingredients (a) a non-steroidal anti-inflammatory selected from the group consisting of aspirin and ibuprofen and (b) a diuretic selected from the group consisting of pamabrom and hydrochlorothiazide, these ingredients being present at a level in these compositions to afford relief from the symptoms of dysmenorrhea and/or premenstrual syndrome when said compositions are administered to subjects exhibiting these conditions. As an alternative, the compositions of this invention may contain as an extra pharmaceutically active ingredient an antihistamine and particularly pyrilamine or a pharmaceutically acceptable salt thereof. Pyrilamine has been shown to be a safe and effective calmative, relieving the tension of dysmenorrhea and/or premenstrual syndrome. These products have the virtue of containing effective anti-inflammatory agents and high potency diuretics and in the alternative, also an effective calmative and at the same time limiting to a minimum the drugs that the individual will be exposed to.

As indicated above, the non-steroidal anti-inflammatory agents that are useful for the present purposes are ibuprofen or aspirin. Combinations of these drugs may also be employed but ordinarily either one or the other will be utilized. The quantity of said anti-inflammatory agent that will be contained in the present composition may be expressed in the form of the daily average for this agent. The daily average dose for the non-steroidal anti-inflammatory agent contained in the products of this invention will vary with anti-inflammatory drug selected. Generally for ibuprofen this will be about 100 mg to about 2 gm with the preferred range being about 200 mg to about 800 mg. In the case of aspirin the general average daily dose will be about 200 mg to about 5 gm. The preferred range being about 500 mg to 2 gm.

In a similar fashion, the quantity of the particular diuretics of use in the present invention and contained in the present products may also be expressed on the basis of the daily average dose for the diuretics (i.e. pamabrom, hydrochlorothiazide or combination thereof). In this case, likewise, the daily average dose for the diuretic contained in the product will vary with the particular diuretic selected. When the diuretic is hydrochlorothiazide the general average daily dose for this drug contained in the product will be from 5 mg to about 250 mg and in the case of pamabrom 5 mg to about 500 mg. In both cases the preferred range is about 25 mg to about 200 mg.

When the antihistamine (i.e. pyrilamine or its pharmaceutically acceptable salts) is employed in the practice of this invention its level of use is also expressible on the basis of its daily average dose. In this case, the daily average dose will be from about 15 mg to about 400 mg. However, the preferred daily average dose for the antihistamine will fall in the range of from about 30 mg to about 200 mg.

Any of the pharmaceutically acceptable salts of pyrilamine may be utilized in carrying forward the purpose of this invention. By way of example mention may be made of pyrilamine maleate citrate, hydrochloride or sulfate.

The products of this invention will generally be administered in a convenient unit dosage form. The quantity of the respective ingredients that may be contained in this unit dosage form is given in the table below:

| | Unit Dosage | |
|---|---|---|
| | General Range in mg. | Foem Preferred Range in mg. |
| Ibuprofen, | 50 mg to 1000 mg | 100 mg to 500 mg |

-continued

| | Unit Dosage | |
|---|---|---|
| | General Range in mg. | Foem Preferred Range in mg. |
| Aspirin or combinations | | |
| Pamabrom, Hydrochlorothiazide or combinations | 1 mg to 100 mg | 5 mg to 50 mg |
| Pyrilamine Salt | 0 mg to 100 mg | 15 mg to 50 mg |

Optimally each unit dosage form will contain from about 200 mg to about 400 mg of ibuprofen or from about 325 to 500 mg of aspirin.

In addition to the pharmaceutically active ingredients mentioned about the products of this invention may also contain other ingredients. These to a large extent will depend on the nature of the unit dosage form that is selected for dispensing the present composition.

The present products may be made into capsules, tablets, powders, caplets and may be film coated, enteric coated or formulated into sustained release dosage forms or liquid dosage compositions. When formed into tablets or caplets they may contain adjuvants that facilitate the tableting of the product or enhance its elegance or dissolution rates. Generally illustrative of the adjuvants that may be contained in the various dosage forms encompassed in the present invention the following may be mentioned; disintegrating agents, binders, lubricants, fillers, glidents, surfactants, flavoring agents, sweeteners, solvents, liquid carriers, suspending agents, preservatives, etc. More particularly the adjuvants that may be contained in the various dosage forms over and above the active ingredients are as follows:

Caplet and Tablet: Cellulose, lactose, corn starch, stearic acid, water, gelatin, talc, sterotix, magnesium stearate, terra alba, sucrose, agar, pectin, Cab-O-Sil, acadia, etc.

Capsule: spray dried lactose, dimethylsiloxane, corn starch, water, magnesium stearate, sucrose, agar, pectin, cab-o-sil, etc.

Liquid Dosage Forms: polyethylene glycol, sucrose, povidone, sodium citrate, citric acid, flavor, color, quinine, salicylic acid, water, peanut oil, olive oil, sesame oil, etc.

Sustained release compositions may contain such things as glyceryl monostearate or glyceryl distearate.

In general, the products of the present invention may be prepared using the standard technique well known to those skilled in this art e.g. standard tableting or capsule preparing procedures. However, when pamabrom is utilized as the diuretic and ibuprofen as the non-steroidal anti-inflammatory it has been found advantageous to granulate the pamabrom before mixing it with the ibuprofen. These ingredients, when mixed together in standard procedures tend to form eutectic mixtures with the result that tablets containing such a mixture become soft upon exposure to stress testing conditions and capsules turned pasty. In addition both of these dosage forms also changed color from white to yellow or orange when prepared using the standard procedures.

When an antihistamine e.g. pyrilamine maleate, is used in conjunction with the pamabrom and ibuprofen, it is often advantageous to granulate the combination of pamabrom and antihistamine before mixing this combination with the ibuprofen. This mixture, with or without other adjuvants may then be used to prepare the dosage forms e.g. capsule, tablets.

The products of this invention may be administered using a variety of regimens. Ordinarily the acceptable daily dose will be provided by taking the product twice, three times or four times a day and preferably after meals.

The following examples are given to further illustrate the present invention. It is to be understood, however, that the invention is not limited thereto.

The following are the chemical definitions of the materials used in the Examples and identified therein as their trade designations:

Avicel pH 101 and 102: Microcrystalline Cellulose.

Starch 1500: Pregelatinized starch of Colorcon Inc., West Point, Pa.

Silicone Oil: Dimethicone (U.S.P.), Dimethylpolysiloxane 350 CS, Dow Corning

Tween 80: Polysorbate 80 (CTFA-Cosmetic Ingredient Dictionary, Third Edition, p. 247)

Cab-O-Sil: Fumed Silica

Providone: PVP (CTFA-Cosmetic Ingredient Dictionary, Third Edition, p. 263)

Crospovidone XL10: Cross Linked Polyvinylpyrrolidone, GAF Corp.

The "Ibuprofen Granulation" used in Examples 5 and 6 below is prepared by first mixing ibuprofen (200 mg.) and corn starch (50 mg.) An aqueous granulating solution was prepared containing POVIDONE (K29-32) (6 mg), AVICEL (PH 101) (41.5 mg) and (CROSPORIDONE XL-10 (1.5 mg) which was used to granulate the ibuprofen/starch mixture.

EXAMPLE 1

Ibuprofen/Pamabrom/Pyrilamine Maleate: Capsules Formula CE 3375-70

| Ingredients | Amount Per Dose |
|---|---|
| Ibuprofen | 150.00 mg |
| Pamabrom | 25.00 mg |
| Pyrilamine Maleate | 15.00 mg |
| Avicel pH 101 | 50.00 mg |
| Starch 1500 | 117.50 mg |
| Silicon Oil | 2.00 mg |
| Tween 80 | 0.50 mg |
| Cab-O-Sil | 0.25 mg |
| | 360.25 mg |

Method
A. Blend b, and c
B. Dissolve d in water and use to granulate A, then dry
C. Blend f, g, and h
D. Blend B, C, and 1. Fill into size #1 capsules

EXAMPLE 2

Ibuprofen/Pamabrom: Capsules Formula CS 3570-05

| Ingredients | Amount Per Dose |
|---|---|
| Ibuprofen | 150.00 mg |
| Pamabrom | 25.00 mg |
| Avicel pH 101 | 82.50 mg |
| Starch 1500 | 90.00 mg |
| Silicon Oil | 2.00 mg |
| Tween 80 | 0.50 mg |
| | 350.00 mg |

Method:
A. Mix a, b, and c, granulate with water and dry
B. Mix f, g, and h
C. Mix A, B, d, and e
D. Fill C into size #1 capsules

EXAMPLES 3 AND 4

Ibuprofen/Hydrochlorothiazide HCl: Capsule

| Ingredients | Formula 3570-14 Amount Per Dose | Formula 3570-31 Amount Per Dose |
|---|---|---|
| Ibuprofen | 200.00 mg | 300.00 mg |
| Hydrochlorothiazide HCl | 12.50 mg | 12.50 mg |
| Starch 1500 | 134.50 mg | 183.50 mg |
| Silicon Oil | 2.00 mg | 2.80 mg |
| Tween 80 | 0.50 mg | 0.70 mg |
| Cab-O-Sil | 0.25 mg | 0.50 mg |
| | 349.75 mg | 500.00 mg |

Method:
A. Blend all ingredients
B. Fill blends for CS3570-14 into size #1 capsules and for CS3570-31 into size #0 capsules.

EXAMPLE 5

Ibuprofen/Pamabrom/Pyrilamine Maleate Tablets

| Ingredients | Formula CS3570-34 Amount Per Dose |
|---|---|
| Pamabrom | 25.00 mg |
| Pyrilamine Maleate | 15.00 mg |
| Starch 1500 | 75.00 mg |
| Povidone, USP (K29-32) | 0.75 mg |
| Hydroxypropylmethycellulose E5-Premium | 4.11 mg |
| Propylene Glycol | 0.90 mg |
| Ibuprofen Granulation (Equivalent to 150 mg. Ibuprofen) | 224.24 mg |
| Silicon Oil | 2.00 mg |
| Tween 80 | 0.50 mg |
| Starch 1500 | 35.00 mg |
| | 382.50 mg |

Method:
A. Blend a, b, and c, granulate with water and dry.
B. Dissolve d, e, and f in water and use to spray coat A.
C. Blend h, i, and j.
D. Blend B, C, and g and compress into tablet.
E. Blend a, b, and c
F. Dissolve d in water and use to granulate A, then dry.
G. Dissolve e, f, and g in water and use to spray coat B.
H. Blend C, D, and h and compress into tablet.

EXAMPLE 6

Ibuprofen/Pamabrom/Pyrilamine Maleate Tablets

| Ingredients | Formula 3570-32 Amount Per Dose |
|---|---|
| Pamabrom | 25.00 mg |
| Pyrilamine Maleate | 15.00 mg |
| Avicel PH 101 | 50.00 mg |
| Povidone, USP (K29-32) | 5.60 mg |
| Hydroxypropyl methylcellulose E5-Premium | 6.63 mg |
| Propylene Glycol | 1.24 mg |
| Ibuprofen Granulation (Equivalent to 150 mg. Ibuprofen) | 224.24 mg |
| Starch 1500 | 35.00 mg |
| Silicone Oil | 2.00 mg |
| Tween 80 | 0.50 mg |
| | 366.35 mg |

Method:
A. Blend all ingredients geometrically
B. Compress into tablets

EXAMPLE 7

Ibuprofen/Hydrochlorothiazide HCl Tablets

| Ingredients | Formula 3570-15 Amount Per Dose |
|---|---|
| Ibuprofen | 200.00 mg |
| Corn Starch NF | 50.00 mg |
| Povidone, K29-32 | 6.00 mg |
| Avicel PH 101 | 41.50 mg |
| Avicel PH 102 | 136.50 mg |
| Hydrochlorothiazide HCl, USP | 12.50 mg |
| Crospovidone XL10 | 2.50 mg |
| Cab-O-Sil | 0.50 mg |
| Magnesium Stearate | 0.50 mg |
| | 450.00 mg |

What is claimed is:

1. A pharmaceutical composition for the relief of dysmenorrhea and/or premenstrual syndrome consisting essentially of as the only pharmaceutically active ingredients (a) ibuprofen and (b) pamabrom, said pharmaceutically active ingredients (a) and (b) being present in the composition in amounts effective to afford relief from the symptoms of dysmenorrhea and/or premenstrual syndrome.

2. A pharmaceutical composition according to claim 1 including a pharmaceutical carrier.

3. A pharmaceutical composition according to claim 1 having as an average daily dose from about 100 mg to about 2 gm of ibuprofen and from about 5 mg to about 500 mg of pamabrom.

4. A pharmaceutical composition according to claim 3 in which the average daily dose for said ibuprofen is from about 200 mg to about 800 mg and the average daily dose for said pamabrom is from about 25 mg to about 200 mg.

5. A pharmaceutical composition according to claim 1 in unit dosage form containing from about 50 mg to about 1000 mg of said ibuprofen and from about 1 mg to about 100 mg of said pamabrom.

6. A pharmaceutical composition according to claim 5 in unit dosage form containing from about 100 mg to about 500 mg of said ibuprofen and from about 5 mg to about 50 mg of said pamabrom.

7. A pharmaceutical composition according to claim 1 also containing as an antihistamine, pyrilamine or a pharmaceutically acceptable salt thereof, said antihistamine also being present in said composition at an antihistamine effective level.

8. A pharmaceutical composition according to claim 7 having as an average daily dose from about 100 mg to about 2 gm of said ibuprofen, from about 5 mg to about 500 mg of said pamabrom and from about 15 mg to about 400 mg for said antihistamine.

9. A pharmaceutical composition according to claim 8 having as an average daily dose from about 200 mg to about 800 mg for said ibuprofen, from about 25 mg to about 200 mg of said pamabrom and from about 30 mg to about 200 mg for said antihistamine.

10. A pharmaceutical composition according to claim 7 in unit dosage form containing frm about 50 mg to about 1000 mg of said ibuprofen, from about 1 mg to about 100 mg of said pamabrom and form about 15 mg to about 50 mg of said antihistamine.

11. A pharmaceutical composition according to claim 10 in unit dosage form containing from about 100 mg to about 500 mg of said ibuprofen, from about 5 mg to about 50 mg of said pamabrom and from about 15 mg to about 50 mg of said antihistamine.

12. A pharmaceutical composition according to claims 7, 8, 9, 10 or 11, wherein said antihistamine is pyrilamine maleate.

13. A pharmaceutical composition according to claims 7, 8, 9, 10 or 11, including a pharmaceutical carrier.

14. A process for relieving symptoms of dysmenorrhea and/or premenstrual syndrome in a subject exhibiting such symptoms which comprises administering to said subject a composition of claims 1, 2, 3, 5, 6, 7, 8, 9, 10 or 11 in an amount sufficient to relieve said symptoms.

* * * * *